(12) United States Patent
Rabe Ralam et al.

(10) Patent No.: US 11,112,408 B2
(45) Date of Patent: Sep. 7, 2021

(54) BIOSENSOR FOR DETECTING THE PRESENCE OF BACTERIA

(71) Applicants: Centre National de la Recherche Scientifique (CNRS), Paris (FR); Universite de Montpellier, Montpellier (FR); AXLR, SATT du Languedoc Roussillon (SATT AXLR), Montpellier (FR)

(72) Inventors: Tatiana Rabe Ralam, Montpellier (FR); Arnaud Vena, Saint Mathieu de Tréviers (FR); Mamadou Balde, Campiègne (FR); Brice Sorli, Montagnac (FR); Morgane Nedelec, Balaruc-les-Bains (FR); Héla Bahloul, Montpellier (FR)

(73) Assignees: CENTRE NATIONAL DE LA RECHERCHE SCIENTIFIQUE (CNRS), Paris (FR); UNIVERSITE DE MONTPELLIER, Montpellier (FR); AXLR, SATT DU LANGUEDOC ROUSSILLON (SATT AXLR), Montpellier (FR)

(*) Notice: Subject to any disclaimer, the term of this patent is extended or adjusted under 35 U.S.C. 154(b) by 149 days.

(21) Appl. No.: 16/317,149

(22) PCT Filed: Jul. 12, 2017

(86) PCT No.: PCT/EP2017/067636
§ 371 (c)(1),
(2) Date: Jan. 11, 2019

(87) PCT Pub. No.: WO2018/011315
PCT Pub. Date: Jan. 18, 2018

(65) Prior Publication Data
US 2019/0257831 A1 Aug. 22, 2019

(30) Foreign Application Priority Data
Jul. 12, 2016 (FR) .................................. 1656702

(51) Int. Cl.
| | | |
|---|---|---|
| *A61K 48/00* | (2006.01) | |
| *C07H 21/02* | (2006.01) | |
| *G01N 33/569* | (2006.01) | |
| *G01N 31/22* | (2006.01) | |
| *G01N 33/02* | (2006.01) | |
| *G01N 33/58* | (2006.01) | |
| *C12Q 1/02* | (2006.01) | |
| *C12N 15/113* | (2010.01) | |
| *C12N 15/11* | (2006.01) | |
| *C12N 15/115* | (2010.01) | |

(52) U.S. Cl.
CPC ...... *G01N 33/56911* (2013.01); *C12N 15/111* (2013.01); *C12N 15/113* (2013.01); *C12N 15/115* (2013.01); *C12Q 1/02* (2013.01); *G01N 31/22* (2013.01); *G01N 31/229* (2013.01); *G01N 33/02* (2013.01); *G01N 33/58* (2013.01); *C12N 2310/16* (2013.01)

(58) Field of Classification Search
CPC .......................... C12N 15/115; C12N 2310/16
See application file for complete search history.

(56) References Cited

U.S. PATENT DOCUMENTS

| | | | | |
|---|---|---|---|---|
| 6,974,669 | B2 * | 12/2005 | Mirkin ................. | C12Q 1/6834 435/5 |
| 8,852,893 | B2 * | 10/2014 | Shuber ............... | G01N 33/5308 435/91.2 |
| 2002/0072079 | A1 * | 6/2002 | Woodaman ............ | G01N 33/12 435/7.32 |
| 2004/0018641 | A1 | 1/2004 | Goldsmith et al. | |
| 2011/0097715 | A1 | 4/2011 | Siret et al. | |
| 2013/0137085 | A1 | 5/2013 | Livache et al. | |
| 2015/0292994 | A1 | 10/2015 | Baril et al. | |
| 2015/0322494 | A1 | 11/2015 | Navarro Y Garcia et al. | |

FOREIGN PATENT DOCUMENTS

WO  WO 2015/088455 A1 * 6/2015 ........... C12N 15/115

OTHER PUBLICATIONS

Luo et al. (Electroanalysis, 2012, 24, 5, 1186-1191).*
French Preliminary Search Report dated Apr. 7, 2017, by the French Patent Office in corresponding French Patent Application No. 1656702. (12 pages).
International Search Report dated Jul. 11, 2017, by the European Patent Office in corresponding International Patent Application No. PCT/EP2017/067636 (with English translation). (8 pages).
Deng et al., "Aptamer binding assays for proteins: The thrombin example—A review," Analytica Chimica Acta, (2014), vol. 837, pp. 1-15.
Revzin et al., "Biosensors for immune cell analysis—A perspective," Biomicrofluidics, (2012), vol. 6, No. 2. (13 pages).

* cited by examiner

*Primary Examiner* — Amy H Bowman
(74) *Attorney, Agent, or Firm* — Buchanan Ingersoll & Rooney PC

(57) ABSTRACT

The present invention relates to a biosensor for detecting the presence and/or measuring the concentration of at least one biological agent, comprising a support on which a barcode is disposed, at least one area of which is functionalised by at least one aptamer capable of selectively immobilising said biological agent, said aptamer per se being directly or indirectly bonded to a pigment molecule capable either of producing colour, or of changing colour following the immobilisation of the biological agent by said aptamer.

27 Claims, 3 Drawing Sheets

Specification includes a Sequence Listing.

Nanoporous alumina support

↓ Functionalization and immobilization of the aptomers

Functionalized support

Cephalosporin + Fluorochrome

Biosensor-Dynamic 2D barcode

BIOSENSOR FOR DETECTING THE PRESENCE OF BACTERIA

CROSS-REFERENCE TO RELATED APPLICATIONS

This application is a U.S. National Stage Application pursuant to 35 U.S.C. § 371 of International Patent Application PCT/EP2017/067636, filed on Jul. 12, 2017, and published as WO 2018/011315 on Jan. 18, 2018, which claims priority to French Patent Application 1656702, filed on Jul. 12, 2016, all of which are incorporated herein by reference in their entireties for all purposes.

The present invention relates to a biosensor for detecting the presence and/or measuring the concentration of at least one biological agent, in particular bacteria, and also a method for analyzing the contamination by at least one biological agent in an environment employing said biosensor.

In the hospital sector, there are devices which make it possible to detect the presence of bacteria, based on searching for bacteria in samples from a patient, in culture and antibiogram, but also based on methods such as PCR and API strips. Mention may be made of the Singlepath® rapid pathogen detection tests sold by Merck and the bacterial detection kits sold by Zayho.

However, these devices require an incubation and culture time of the sample ranging from 24 h to 48 h, which delays the detection of the infection and therefore postpones effective treatment of the patient with consequences that can be serious for them. In addition, these devices must be stored between 2° C. and 8° C. before use and are generally only able to detect a single species of bacteria.

In the agri-food sector, there are devices for detecting the presence of bacteria in food packaging, implementing a dynamic barcode, that is to say capable of changing in the presence of bacterial metabolites.

However, these devices make it possible to detect the presence of bacteria only indirectly and not immediately.

Furthermore, documents US2002/0072079 and US2004/018641 disclose contamination detectors which make it possible to identify a contamination comprising: a first coded index for identifying a product, a second coded index for identifying a condition indicative of a contamination, an indicator of contamination associated with a first and a second barcode and means for changing the appearance of the indicator in the presence of a contamination condition, wherein the means for changing the appearance of the indicator modify the appearance of the first and second coded index.

However, these documents do not report a color generation or a colorimetric change through the presence of a coloring molecule linked to an aptamer.

In addition, the devices of the prior art do not make it possible to provide immediate information regarding the concentration of a biological agent in a sample; in particular, they do not make it possible to determine whether the infectious dose has been exceeded or not, namely if the sufficient amount of pathogen to cause disease has been exceeded or not.

There is therefore a need for a device which makes it possible to overcome the deficiencies of the bacterial detection devices of the prior art.

The present invention thus aims to provide a device for detecting the presence and/or measuring the concentration of at least one biological agent that does not have the limitations of the existing devices.

In particular, the present invention aims to provide a device which makes it possible to detect the presence of at least one biological agent, and preferably several different biological agents, more quickly than the devices of the prior art, or even immediately.

The present invention also aims to provide a device which makes it possible to provide information regarding the concentration of at least one biological agent, and preferably several different biological agents, in a sample more quickly than the devices of the prior art, or even immediately.

FIGURES

FIG. 2 illustrates the use of the biosensor from body fluids. The information received via the dedicated mobile application may allow: 1. Identification of the pathogens present in the sample, 2. Estimation of the corresponding amount, 3. The specific antibiogram for each pathogen, 4. Determination of the infectious dose and 5. Localization.

BIOSENSOR

According to a first subject, the present invention relates to a biosensor for detecting the presence and/or measuring the concentration of at least one biological agent, comprising a support on which a barcode is placed, at least one area of which is functionalized by at least one aptamer capable of selectively immobilizing said biological agent, said aptamer itself being linked, directly or indirectly, to a coloring molecule able either to produce color or to change color following the immobilization of the biological agent by said aptamer, optionally by activation by flash, as described in detail in the description below.

According to a particular embodiment, the coloring molecule is linked, directly or indirectly, via a labile bond.

Operating Principle

The operating principle of the device according to the invention is based on a colorimetric phenomenon, which makes it possible to signal the detection of the targeted biological agent in a simple, direct and immediate manner.

The device of the present invention is specific to at least one biological agent, that is to say that it detects only the biological agent(s) it is intended to detect, namely the targeted biological agent(s).

The surface of the device according to the invention comprises, according to a particular embodiment, a barcode, at least one area of which is able to produce a color or to change color after said zone has been brought into contact with the targeted biological agent and after said biological agent has been immobilized by the aptamers.

As described in detail below, color generation or color change may be associated with the release, by the biological agent, of particular enzymes, caused by the biological agent-aptamer bonding.

According to a first variant, this attack of particular enzymes may cause a labile bond present between the coloring molecule and the aptamer to break.

According to a second variant, this attack of particular enzymes may cause a color generation or a color change of the coloring molecule.

According to a third variant, this attack of particular enzymes may be the source of these two phenomena at the same time, namely the breaking of a labile bond present between the coloring molecule and the aptamer and color generation or a color change of the coloring molecule.

Thus, as illustrated in the examples, the inventors have demonstrated that a coloring molecule-aptamer bond comprising a β-lactam unit was broken down as a result of release of β-lactamase following the immobilization of two types of bacteria (see implementation in example 3) on the aptamer, causing the release of the coloring molecule and consequently allowing a color generation and the formation of a 2D barcode indicating the presence of the corresponding bacteria.

Hence, according to this particular variant, the surface of the device according to the invention comprises a barcode, at least one area of which is able to release a coloring molecule when said area comes into contact with the targeted biological agent and when said biological agent is immobilized by the aptamers.

Another variant, based on the same principle, makes it possible to replace the antibiotic molecule with another type of molecule, capable of being attacked by different enzymes. Mention may be made, for example, of the lactose/β-galactosidase pair, within which β-galactosidase may be secreted especially by $E.\ coli$. Mention may also be made of the use of α-amylase, a fungal enzyme, produced especially by Thermomyces lanuginosus, capable of attacking polysaccharides, especially in order to make them fermentable.

The inventors have also illustrated in the examples the variant according to which the coloring molecule is not released but is able to generate a color or a color change of said coloring molecule following the immobilization of a bacterium on the aptamer (examples 4 and 5).

Coloring Molecule-Aptamer Bond

According to the first variant of the invention described above, the coloring molecule may, for example, be released after the biological agent has been immobilized by the aptamer. In this case, the coloring molecule is linked to the aptamer, for example via a second spacer as will be described in detail below, and the coloring molecule may be attached to this second spacer by means of a labile bond.

According to the second variant of the invention described above, the coloring molecule may not be released after the biological agent has been immobilized by the aptamer but may however change color after the biological agent has been immobilized by the aptamer.

Advantageously, again according to this second variant, the bond between the coloring molecule and the aptamer may not comprise a labile bond or a spacer. According to a particularly advantageous embodiment, the coloring molecule belongs to the family of antibiotics.

The principle of detection of this invention is based on a color change resulting from an inducible chain reaction. Indeed, in the case of a health application for the detection of nosocomial diseases, and if the biological sample to be tested contains the target bacterium or bacteria, the aptamer recognizes the biological agent and immobilizes it.

The bacterium is then brought into contact with the antibiotic molecule bonded to the 3' end of the aptamer. Following this contact, and if the bacterium is resistant to the antibiotic used (family of cephalosporins, penicillins for example), said bacterium produces enzymes, for example β-lactamases, that are able to attack the antibiotic. As units that may belong to these antibiotics and that may be attacked by β-lactamases, mention may be made of β-lactam rings.

All β-lactam antibiotics, namely those containing a β-lactam ring, are suitable for the implementation of the invention. In this respect, mention may especially be made of penicillin derivatives (penams), cephalosporin derivatives (cephems), oxapenems, monobactams and carbapenems.

Depending on the nature/family of the antibiotic and depending on the mode of detection, a colorimetric reaction takes place.

According to a particular embodiment of the invention, the colorimetric reaction may especially cause luminescence, for example fluorescence.

Thus, according to a first particular embodiment, the present invention relates to a biosensor for detecting the presence and/or measuring the concentration of at least one biological agent, comprising a support on which a barcode is placed, at least one area of which is functionalized by at least one aptamer capable of selectively immobilizing said biological agent, said aptamer itself being linked, directly or indirectly, to a coloring molecule via a labile chemical bond which is able to break following immobilization of the biological agent by said aptamer, and said coloring molecule being non-luminescent in its form linked to the aptamer and luminescent, preferably fluorescent, in its form not linked to the aptamer.

It also relates, according to another particular embodiment, to a biosensor as defined above, wherein the coloring molecule is covalently bonded to the aptamer via a second spacer, said second spacer being linked to the coloring molecule by a labile chemical bond which is capable of breaking following immobilization of the biological agent by the aptamer, for example a labile chemical bond capable of breaking in the presence of a β-lactamase.

It also relates, according to another particular embodiment, to a biosensor as defined above, wherein the coloring molecule is an antibiotic covalently bonded to the aptamer, said coloring molecule being capable of producing a color or of changing color following immobilization of the biological agent by the aptamer, for example said chemical molecule comprising a chromogenic antibiotic.

Aptamer/Biological Agent

In the context of the present invention, the term "aptamer" is intended to mean a synthetic oligonucleotide capable of selectively binding a ligand contained in the targeted biological agent (typically present on the surface of the targeted biological agent) or else secreted or excreted by said agent, that is to say the biological agent that it is desired to detect using the biosensor of the invention.

Aptamers are generally synthetic compounds, isolated in vitro from combinatorial libraries of a large number of randomly sequenced compounds by an iterative selection method referred to as SELEX.

One of the advantages of the device of the invention is that it makes it possible to detect any biological agent, as long as there is an aptamer specific to said biological agent.

Indeed, it is sufficient to vary the aptamer to target a particular biological agent. In other words, the device is based on a specificity in terms of the biological agent/aptamer pair.

The biological agent is typically selected from the group consisting of bacteria, prions, viruses, mycotoxins and peptides.

According to a preferred embodiment, the biological agent is a bacterium and the aptamer is capable of selectively binding at least one membrane protein of said bacterium, chosen for example from lipopolysaccharides (LPS) and peptidoglycans (PPG).

The device of the invention is particularly suitable for detecting nosocomial infections in the hospital environment, or else for detecting bacterial contamination in the agri-food domain, detecting pathogens in water in drinking water distribution networks, rivers, lakes or even swimming pools.

Preferably, the biological agent is a bacterium selected from the group consisting of *Escherichia coli, Pseudomonas aeroginosa, Acinetobacter baumannii, Staphylococcus aureus, Clostridium difficile, Clostridium botulinum, Streptococcus pneumoniae, Treponema pallidum, Salmonella gastroenteretis, Listeria monocytogenes* and *Legionella* spp.

When the biological agent is a bacterium, and as indicated above, the present invention may advantageously take advantage of the presence of an antibiotic molecule in the device, causing the secretion of enzymes by the bacterium, the secretion of said enzymes enabling, directly or indirectly, the generation of a color or a color change via the coloring molecule.

In accordance with the first variant described above, the antibiotic molecule is included in a spacer between the aptamer and the coloring molecule or "second spacer" in the context of the present invention.

Still according to this first variant, a labile chemical bond is included between the spacer and the coloring molecule. In other words, the attack of the enzyme secreted by the chemical bond between the aptamer and the coloring molecule causes the release of the coloring molecule, generating a color or causing a color change.

According to the second variant described above, the coloring molecule comprises or consists of an antibiotic molecule that is able to change color, or chromogenic antibiotic, following the attack of the enzymes originating from the target bacterium captured by the biosensor according to the invention.

The aptamers used in the device of the invention can be of any kind, as long as they are able to selectively immobilize the biological agent that it is desired to detect, as long as they can be attached to the support of the device, for example via a first spacer, and as long as they can be linked to a coloring molecule, for example via a second spacer.

As explained above, a labile bond may be between the coloring molecule and the aptamer, in particular between the second spacer, itself comprising an antibiotic molecule, and the coloring molecule. Alternatively, such a labile bond may not be between the coloring molecule and the aptamer in the case in which the coloring molecule belongs to the family of antibiotics and is able to generate color or cause a color change or chromogenic antibiotic. In the latter case, the coloring molecule may be directly linked to the aptamer, without requiring the presence of a second spacer.

Starting from the aptamers described in the literature and in databases, those skilled in the art will be able to modify them in order to enable the attachment thereof to the support of the device and the bonding thereof with a coloring molecule, using conventional techniques of surface functionalization and covalent coupling, and especially via a second spacer.

Preferably, the aptamer is a strand of RNA or DNA. It may also be a peptide.

According to a particular embodiment, the aptamer is modified on its 3' end, in particular to bear a —COOH function.

According to another particular embodiment, the aptamer is modified on its 5' end, in particular to bear an —$NH_2$ function.

This modification makes it possible to readily attach the aptamer to the support of the device, that is to say with the customary techniques for grafting to a support.

The aptamer may thus be covalently bonded to the barcode area via a first spacer.

According to a particular embodiment, said first spacer may have the formula —S—$(CH_2)_n$—C(O)— where n is an integer from 2 to 6 and wherein the sulfur atom is covalently bonded to the support and the carbon atom of the C(O) group is covalently bonded to a nitrogen atom of the aptamer.

According to other particular embodiments, the aptamer-support bond may be made by silane (OH-Silane-$NH_2$), for example TPM, by a heterobifunctional linker (SH-Heterobifonctionnel-$NH_2$), for example SMCC or else by UV. In this regard, producing a silane film on a support with OH bonds has been described in M. Zain et al, "Effect of surface treatments on the durability of green polyurethane adhesive bonded aluminium alloy" International Journal of Adhesion & Adhesives 55 (2014) 43-55, which may be utilized in the context of the present invention. Mention is also made of the article by Y. Guo et al. "Potent antigen-specific immune response induced by infusion of spleen cells coupled with succinimidyl-4-(N-maleimidomethyl cyclohexane)-1-carboxylate (SMCC) conjugated antigens'" International Immunopharmacology 31 (2016) 158-168, which discloses an example illustrating the bonding of a cell via an SH and a protein via an $NH_2$.

The use of molecules belonging to the family of silanes is based on the spontaneous self-assembly of these molecules on surfaces by adsorption, thus organizing themselves into ordered molecular monolayers. This assembly of molecules creates a strong and stable molecular organization. In the context of the present invention, the chosen molecule(s) must contain a head group having high affinity with the hydroxyl end of the substrate, thus enabling anchoring of the molecule to the surface thereof, and an end group that interacts with the 5' $NH_2$ end of the aptamer.

There are different families of molecules, the properties of which correspond to those mentioned above such as organosilanes, thiols and phosphonates. By way of example of organosilane, mention may be made of 3-(trimethoxysilyl)propyl methacrylate (TPM) (PubChem ID: 17318).

The head group of TPM, "RO—Si" reacts, then, with the hydroxyl end (OH) of the substrate. This reaction, referred to as hetero-condensation reaction, results in the formation of a covalent bond of O—Si—R' type, where R' represents the end group which in turn interacts with the 5' $NH_2$ end of the aptamer.

Another type of agent is of heterobifunctional linker type. These are the most noteworthy and the most useful protein conjugation reagents because they have two distinct reactive groups. They have the particular feature of having different reactive groups at the ends.

For example, N-succinimidyl 3-[2-pyridyldithio]propionate (SPDP) or succinimidyl-4-(N-maleimidomethyl)cyclohexane-1-carboxylate (SMCC) (PubChem ID: 125175). SMCC reacts via its maleimide group which is a reactive sulfhydryl (thiol; —SH) group and its NHS end which is amine reactive ($NH_2$), thereby forming stable covalent bonds.

Other molecules belonging to this family of "linkers" can be used provided they have the same groups at the ends, according to techniques well known to those skilled in the art.

This type of grafting can be carried out using techniques known to those skilled in the art, as described in the examples detailed below.

Thus, the device of the invention may in particular implement aptamer/biological agent pairs according to databases well known to those skilled in the art. By way of nonlimiting illustration, mention may be made of the following particular pairs, summarized in the table below:

| Bacterial strain | Aptamer |
|---|---|
| Escherichia coli ATCC 8739 | 5'CGC GTC CCC CGC CGG GCG CGC GCC AGG ATC GAC 3' (SEQ ID NO: 1) |
| Escherichia coli 0157 H7 | 5'CTT CTG CCC GCC TCC TTC CTA GCC GGA TCG CGC TGG CCA GAT GAT ATA AAG GGG TCA GCC CCC CAG GAG ACG AGA TAG GCG GAC ACT 3' (SEQ ID NO: 2) |
| Staphylococcus aureus | 5'TCC CTA CGG CGC TAA CGC CAC CGT GCT ACA ACT CGG ATT 3' (SEQ ID NO: 3) |
| Escherichia coli 0157 H7 | 5'GTC TGC GAG CGG GGC GCG GGC CCG GCG GGG GAT GCG 3' (SEQ ID NO: 4) |

Coloring Molecule

In the device of the invention, the coloring molecule signals the detection of the targeted biological agent, for example by the release of said coloring molecule, as described above in association with one of the particular embodiments of the invention.

In the context of the present invention, the term "coloring molecule" is intended to mean any molecule capable of either producing a color or of causing a color change following a stimulus in its environment. Said stimulus is advantageously represented in the context of the present invention by the immobilization of the biological agent by the aptamer. However, the color generation or color change may be indirectly caused by this immobilization, as explained above. In other words, the present invention also includes the cases in which chain reactions occur from this immobilization, at least one of which causes this color generation or color change via the coloring molecule. The nature of the coloring molecule is described in detail below.

In the context of the present invention, the term "color generation" is intended to mean the appearance of a color relative to the color present in the same area before the biological agent is brought into contact with the biosensor according to the invention, determined relative to a given colorimetric system.

In the context of the present invention, the term "color change" is intended to mean a change in color relative to the color present in the same area before the biological agent is brought into contact with the biosensor according to the invention, determined relative to a given colorimetric system. This color change also includes a contrast change. Hence, the coloring molecule should be selected such that said change after immobilization of the biological agent on the aptamers causes a minimum colorimetric displacement or colorimetric shift in order for it to be detectable by a suitable reading means.

The term "color change" includes the production of luminescence, as will be described below.

As colorimetric system that may be used in the context of the present invention, mention may especially be made of the RGB model. The RGB model is based on three primary colors which, by mixing them, form all the others (256 levels on each channel). Mention may also be made of the HSL model (Hue, Saturation, Lightness), or else the HSV model (Hue, Saturation, Value), which is a derivative of RGB. The latter two enable better understanding or control of the lightness.

Any type of apparatus designed to detect these color generations and/or color changes may be used, according to techniques well known to those skilled in the art.

It should also be noted that in the context of the present invention, colorimetric system is intended to mean not only the trichromatic spaces, since the invention also relates to detection by monochromatic or bichromatic hue change, including in the shades from white to black. This embodiment may in particular correspond to an application in which the barcode is a 1D or 2D barcode.

The following description illustrates the "activation by flash" as used in the context of the present invention according to the embodiment in which the coloring molecule is luminescent, and more particularly fluorescent. This step occurs at the time of reading the result.

According to this embodiment, a second spacer is bonded 3' to the aptamer and is also bonded to a luminescent dye, more particularly one which is photoactivatable. This dye makes it possible, after excitation thereof according to a specific wavelength, to read the detection result. Indeed, in the case of a health application for the detection of nosocomial diseases, and if the biological sample to be tested contains the target bacterium or bacteria, the aptamer recognizes the biological agent and immobilizes it. The bacterium is brought into contact with the antibiotic molecule bonded to the 3' end of the aptamer.

Following this contact, and if the bacterium is resistant to the antibiotic used, for example the family of cephalosporins or penicillins, said bacterium produces enzymes, for example β-lactamases, which attack the antibiotic, for example the β-lactam ring. This induces cleavage of the labile bond between the end of the antibiotic and that of the dye, thereby causing the release of the dye. This dye is excited at a specific wavelength by a mobile phone flash, thus enabling the appearance of the luminescence of the initially colorless dye. In this embodiment, the use of a non-chromogenic antibiotic is preferred.

According to a particular embodiment, the coloring molecule is a chemical molecule and is not an antibody.

As non-luminescent coloring molecule, mention may especially be made of the chromogenic antibiotics of the cephalosporin family, for example nitrocefin and penicillins.

According to a particular embodiment of the invention, the coloring molecule is non-luminescent in its form linked to the aptamer and luminescent, preferably fluorescent, in its form not linked to the aptamer.

As luminescent coloring molecule, and in particular one which is fluorescent, mention may especially be made of 5-FAM, 6-FAM, ATTO-type dyes, especially ATTO 532 or ATTO 550, ATTO 647, DY-510XL, DY-530, HEX, CAL Fluor Orange 560, and in particular ATTO, as implemented in the examples.

Still according to this particular embodiment for which the coloring molecule is luminescent and even more particularly fluorescent, the coloring molecule is not luminescent when it is still linked to the aptamer, which means that the area of the device which is functionalized with the aptamer does not generate any colorimetric phenomenon if it is not in the presence of the targeted biological agent.

is bound to the coloring molecule by a labile bond. It is advantageously formed at least in part by an antibiotic molecule causing the formation of an enzyme precisely capable of attacking said antibiotic molecule, and especially the β-lactam ring. It is this particular embodiment which is illustrated in the examples, by implementing a second spacer comprising cephalosporin. Thus, an aptamer-[cephalosporin]-[ATTO] complex is formed which may be grafted onto a support to give the desired biosensor, enabling the detection of specific bacteria.

As an illustration of such an aptamer-[cephalosporin]-[ATTO] complex, diagram 1 below shows an aptamer-cephalosporin-ATTO647 sequence.

Diagram 1

On the other hand, when it is activated following immobilization of the biological agent, or more particularly released following immobilization of the biological agent, it becomes luminescent and generates a colorimetric phenomenon which can be visualized by a suitable reading means.

This operation ensures the direct and instantaneous detection of the targeted biological agent.

Preferably, such a luminescent coloring molecule has a light absorption band of from 600 nm to 700 nm, preferably from 640 nm to 670 nm, and a light emission band of from 600 nm to 700 nm, preferably from 665 nm to 675 nm or a minimum colorimetric shift for detection.

As a reading means, mention may in particular be made of a film camera or a camera or else a photosensitive sensor of CCD or CMOS type. This last type of sensor combines the three primary colors RGB to create a color image by additive synthesis.

The coloring molecule as described above may be linked to the aptamer by different types of spacers as previously described or directly linked to the aptamer when the coloring molecule comprises the antibiotic.

Thus, the coloring molecule may be linked to the aptamer via a second spacer.

Moreover, as has also been indicated previously, this second spacer may comprise at least one labile bond so as to be able to release the coloring molecule which may thus cause color generation or a color change once free.

The release of the coloring molecule may be triggered by various mechanisms.

According to the embodiment in which the biological agent is a bacterium producing an enzyme of β-lactamase type, and the coloring molecule comprises a ring sensitive to the production of this enzyme, as described above, the labile bond is located between the coloring molecule and the antibiotic.

According to a particular embodiment of the invention, when the biological agent is a bacterium, the second spacer For the purposes of the present invention, the labile bond is advantageously included between the coloring molecule and the second spacer. It is defined in the context of the present invention as being a bond that is capable of being broken following the attack of the spacer arm by the enzyme secreted by the biological agent and especially the bacterium, and more particularly the β-lactam ring included in the antibiotic molecule included in the second spacer arm.

As described above, in the context of this particular embodiment, during the immobilization of said bacterium on the aptamers, the biological agent, and for example the targeted bacterium, is brought into contact with the second spacer providing the connection with the coloring molecule, for example linked 3' or 5' to the aptamer.

Following this contact, if the bacterium is resistant to the antibiotic molecule used, said bacterium produces enzymes capable of attacking at least one bond between the aptamer and the coloring molecule. When, as in the examples, this is a bacterium producing β-lactamases by reaction to an antibiotic action, said bacterium attacks the β-lactam unit present in the cephalosporin included in the second spacer.

Depending on the nature of the antibiotic, the detectable change may be manifested by color generation or color change. This manifestation may be due to the breaking of the labile bond. The coloring molecule released in this way enables the result to be read.

Regardless of the nature of the dye or the antibiotic, the chain reaction results in color changes, which may be translated for example on a dynamic barcode.

Thus, in the case of the detection of bacteria responsible for nosocomial infections, a preferred mode of release of the invention is based on the antibiotic resistance of the bacteria, in particular on resistance to antibiotics of β-lactam type.

Bacteria resistant to antibiotics of β-lactam type have the ability to release β-lactamases when they are in the presence of said antibiotics, which alters the structure of these antibiotics and renders them ineffective.

Preferably, the second spacer is a divalent radical comprising a β-lactam unit, for example a cephalosporin unit.

According to a particular embodiment of the invention, the immobilization of the biological agent, and especially of a bacterium, on the aptamers, results, following a chain reaction, in the breaking of a labile bond which connects the aptamer to a coloring molecule. It is the release of this coloring molecule, which was not luminescent in its form linked to the aptamer but becomes luminescent, preferably fluorescent, when it is released, which causes the colorimetric phenomenon, which appears solely in an area corresponding to the area functionalized by the aptamer.

The appearance of this luminescence therefore modifies the information encoded by the barcode and the reading of the barcode thus modified, using a suitable reading means, then makes it possible to read the information which has been modified relative to the information encoded by the initial barcode, reflecting the detection of the biological agent.

Detection/Application

Any type of detection can be envisaged.

As application type, mention may be made of identification of the bacteria, localization of infectious foci, the antibiogram corresponding to each type of bacteria or else the estimation of the amount present (higher or lower than the infectious dose).

According to one embodiment, it is also possible to measure, using a suitable reading means, the intensity of the color generation or the color change, for example of the luminescence, generated by the coloring molecule, and, by comparison with a predetermined reference value, it is possible to determine whether the concentration of biological agent in the monitored sample is greater than an amount corresponding to a specific infectious dose.

Another advantage of the present invention is that the same reading method may be maintained between pre-immobilization and post-immobilization of the biological agent on the biosensor.

The device or biosensor of the present invention thus makes it possible to detect the presence, and/or measure the concentration, of at least one biological agent in real time, that is to say without prior incubation of the sample to be monitored and without prior treatment, such as lysis in the case of bacteria.

With a rapid detection device, biological agents such as bacteria may be identified before they are incubated and/or proliferate, and may be treated with suitable treatments.

In addition, the device or biosensor of the present invention has the advantage of not requiring specific storage in terms of temperature. In other words, the device of the present invention is thermally stable at a temperature of between −20° C. and 80° C., preferably between 0° C. and 40° C.

Support

The device of the invention has the advantage of being able to be implemented on a wide variety of supports, whether rigid or flexible.

The support may be a flexible or rigid support on which the barcode is placed.

According to one embodiment, the support is a flexible support, preferably a support of paper or plastic type, coated with alumina, paper or plastic.

As plastic material, mention may especially be made of polypropylene or microporous polyethylene as sold under the name Teslin by PPG Industries.

Such supports made of Teslin may especially have a thickness of between 150 μm and 450 μm.

The polypropylene can be hard or semi-rigid.

According to another embodiment, the support is a rigid support, for example made of glass.

Preferably, the support is coated with a layer of alumina on which the barcode is placed.

An alumina layer may be placed by any technique known to those skilled in the art, such as that described in the examples below.

The thickness of the alumina layer typically varies from 500 nm to 10 μm and is for example 1 μm.

The use of the alumina layer has several advantages:

Firstly, an increase in the exchange surface, by virtue of the adaptation of the pore size according to the type of application, but also better adhesion of the chemical functionalization for the attachment of the ligands (aptamers). This is due to the presence of free hydroxide bonds (—OH) at this surface, which will facilitate the immobilization of the aptamers. Thus, the content of available hydroxide bonds may reach approximately 80% for the biosensor.

The use of the alumina layer further has the following advantages:

The alumina layer has thermal stability, such that it does not require any specific storage after its manufacture, it is biocompatible, that is to say it does not degrade the biological material with which it is used, and finally, the manufacturing cost of the alumina layer is relatively low.

Barcode

The device of the invention has the advantage of being able to be implemented with a wide variety of barcodes, whether 1-dimensional or 2-dimensional.

In addition, one or more areas of the barcode may be functionalized with a single aptamer or several different aptamers, in order to be able to detect one or more different biological agents.

Figure 1:
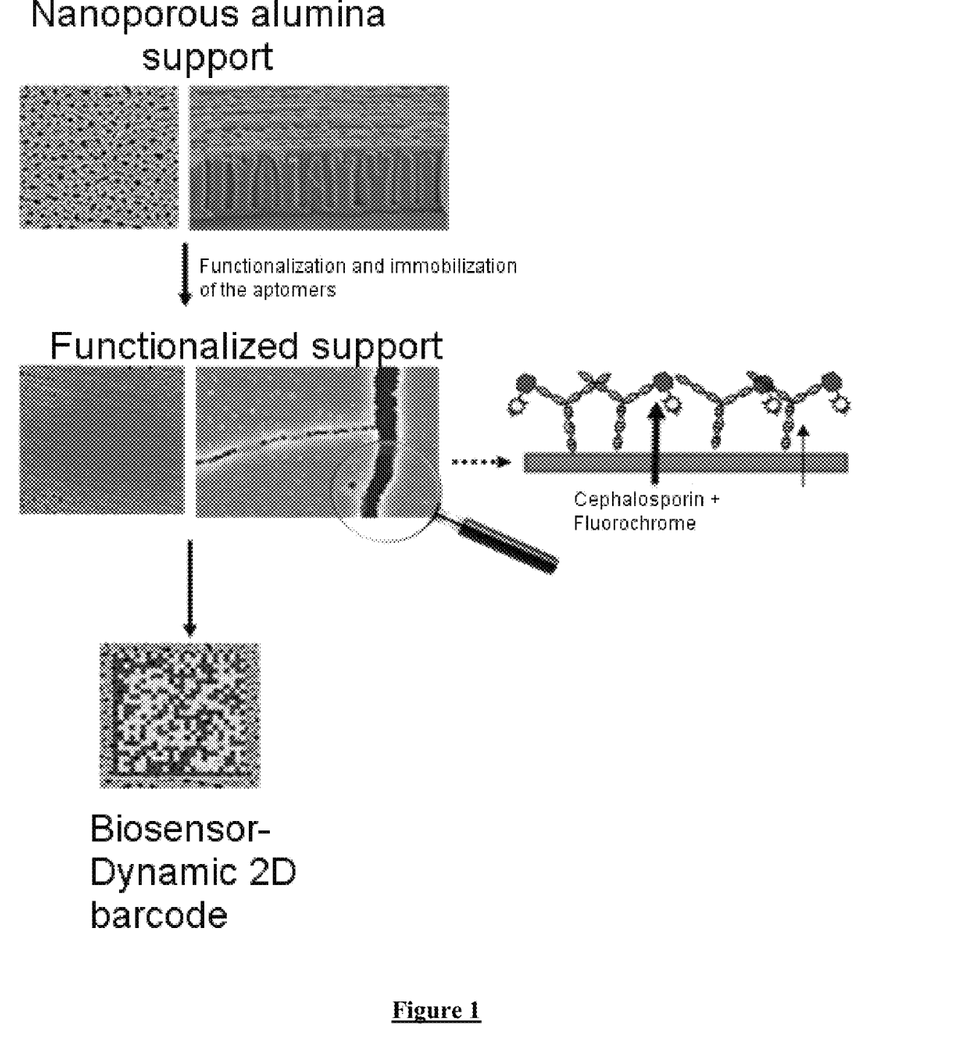
FIG. 1 illustrates the production of the biosensor according to the invention. The biosensor—dynamic 2D barcode makes it possible to detect 5 pathogens.
Figure 2:
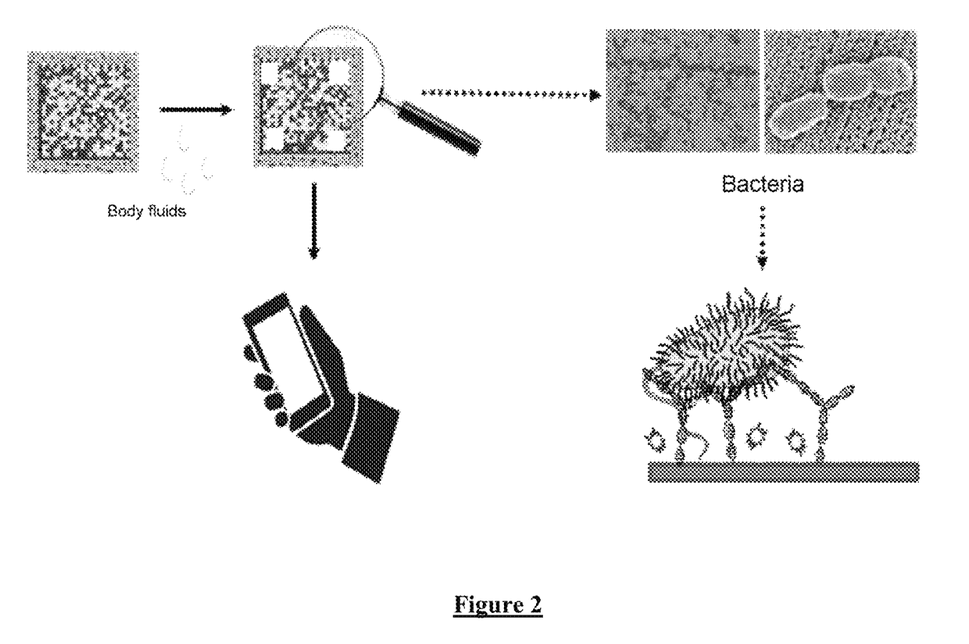
Figure 3:
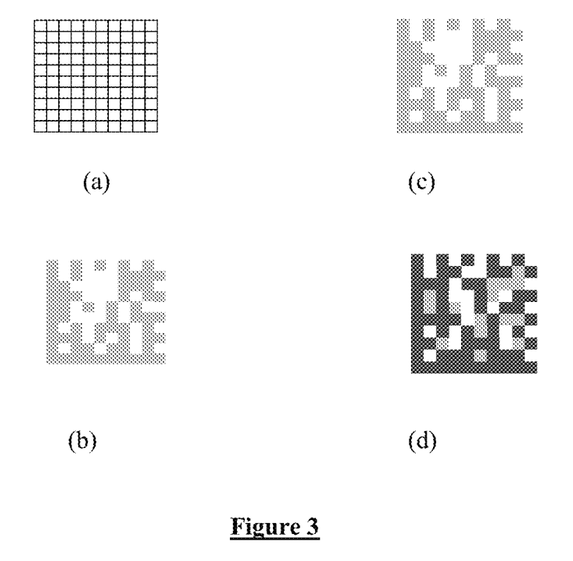
FIG. 3 illustrates the visual evolution of a 2D barcode by changing color hue before and after a target bacterium is revealed by a biosensor according to the invention (example 4.1).
Figure 4:
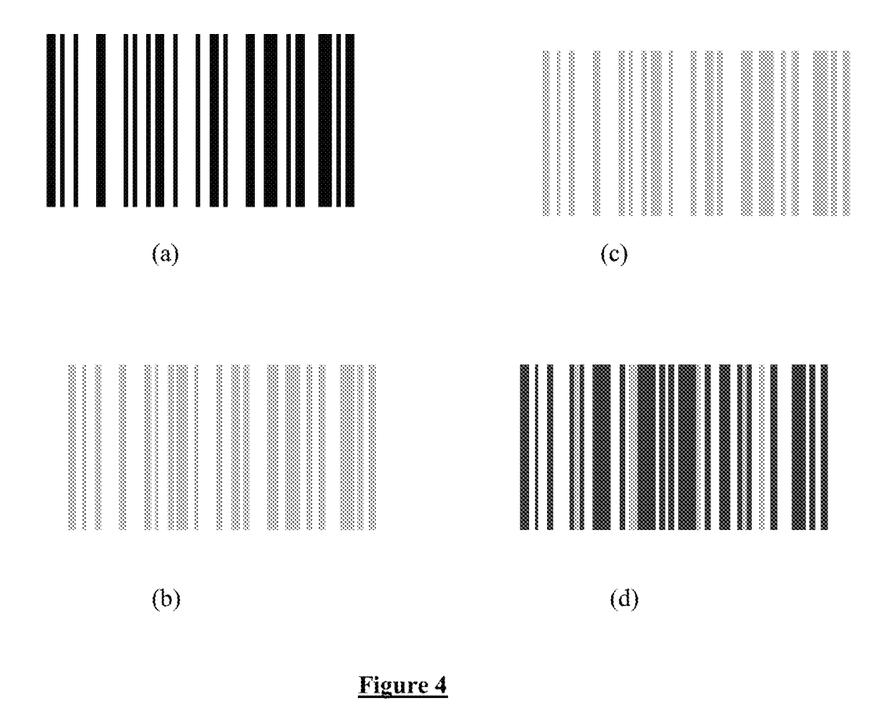
FIG. 4 illustrates the visual evolution of a 1D barcode by changing color hue before and after a target bacterium is revealed by a biosensor according to the invention (example 4.2).

FIGS. 3 and 4 illustrate the use as described in example 4 of 1D and 2D barcodes, in the case of a coloring molecule of chromogenic antibiotic type, nitrocefin, which changes from yellow in the absence of β-lactamase to red in the presence of β-lactamase. As illustrated in this example, the presence of contrasts between the stripes or the pixels makes it possible to carry the message borne by the barcode and to draw conclusions as to the presence or absence of the target bacterium.

According to one embodiment, the barcode is a one-dimensional barcode composed of an assembly of parallel black stripes and white stripes in which at least one area of at least one white stripe or black stripe is functionalized by at least one aptamer.

Preferably, all of at least one white stripe is functionalized by at least one aptamer.

According to variants of this embodiment, two, three, four, or even five or more white stripes may be functionalized with different aptamers, so as to detect two, three, four, or even five or more different biological agents.

According to another embodiment, the barcode is a 2-dimensional barcode composed of an assembly of black pixels and white pixels, in which at least one white pixel or at least one black pixel is functionalized by at least one aptamer.

This type of barcode has the advantage of containing more information, such as the identification of bacteria, the location of infectious foci, the antibiogram corresponding to each type of bacteria and the estimate of the amount present (greater than or less than the infectious dose).

According to variants of this embodiment, two, three, four, or even five or more white pixels may be functionalized with different aptamers, so as to detect two, three, four, or even five or more different biological agents.

Process for Manufacturing the Biosensor

The device of the present invention may be manufactured by techniques giving rise to low production costs.

The device of the present invention may be readily miniaturized and may be produced so as to be single-use and therefore to be destroyed after use.

A support functionalization process suitable for the manufacture of a biosensor according to the invention is described in the examples detailed below.

This process comprises the following steps: preparation of the support, for example comprising coating with a layer of alumina, followed by the optional activation of the layer of alumina to enable grafting of the aptamers, then grafting of the aptamer-coloring molecule complex onto the support, such as activated alumina, or else grafting of the aptamer onto the support, such as activated alumina, followed by grafting of the coloring molecule onto the aptamer thus grafted.

These surface modification steps (coating, activation, functionalization, grafting, coupling, etc.) use techniques known to those skilled in the art.

This process may be implemented to functionalize a predetermined area of a barcode, as illustrated in the examples detailed below, in order to prepare a biosensor according to the invention.

Process for Analyzing a Contamination

According to another subject, the present invention relates to a process for analyzing contamination by at least one biological agent in an environment, comprising at least the steps consisting in:

making available a biosensor according to the invention,
bringing the biosensor into the presence of the environment to be analyzed, under conditions conducive to the immobilization of the biological agent(s) which may be present in said environment by the aptamers of the biosensor,
reading the biosensor thus coated, for example under illumination conditions conducive to the luminescence of the coloring molecule in its form not linked to the aptamer, so as to acquire the information encoded by the barcode of the biosensor thus coated, and
generating, from the acquired information, information regarding the possible presence of at least one biological agent in the environment.

"Environment to be analyzed" is intended to mean the medium in which it is desired to detect the presence of the targeted biological agent.

In the case of the detection of a bacterial contamination in a patient, the device of the invention is typically implemented from body fluids such as, primarily, sweat, urine, saliva or else blood. The device of the invention is therefore not necessarily invasive since it can be implemented on a sample other than blood.

The environment to be analyzed may therefore be a sample of body fluids of a patient such as blood, sweat, urine, or saliva.

In the case of the detection of a bacterial contamination in an agri-food product, this may be the gaseous atmosphere contained in a food packaging or else a sample taken from the surface of or from within the food product, such as wine or beer.

When bringing the biosensor into the presence of the environment to be analyzed, it is ensured that the conditions are conducive to the immobilization of the biological agent(s) which may be present in said environment by the aptamers of the biosensor.

The biosensor may be used at room temperature. Responses are typically obtained in less than 15 to 20 minutes.

When bringing the biosensor into the presence of the environment to be analyzed, if said environment contains biological agents targeted by said biosensor, said agents are immobilized on the aptamers specific to these biological agents, which causes a color generation or a color change, for example because of chain reactions that result in the release of coloring molecules, in the areas corresponding to the areas of functionalization by the aptamers.

The next step therefore consists in acquiring the information encoded by the barcode, either directly by reading the barcode after reaction in the case of a colorimetric reaction, or by exciting the coloring molecule at a wavelength suitable for a luminescent molecule.

Thus, in the particular case of a luminescent coloring molecule, the following step therefore consists in reading the biosensor thus coated under illumination conditions conducive to the luminescence of the coloring molecule in its form not linked to the aptamer, so as to acquire the information encoded by the barcode of the biosensor thus coated.

Those skilled in the art will be able to adapt the illumination conditions to activate the luminescence of the coloring molecule.

According to a preferred embodiment, the luminescence of the coloring molecule is detectable only under stronger illumination than daylight or artificial indoor lighting.

According to this mode, the luminescence of the coloring molecule is typically activated by means of a flash, typically a camera or cell phone flash. Those skilled in the art will be able to adapt the coloring molecule as a function of the wavelength of the flash to take advantage of its luminescence.

In addition to the luminescence conditions, it is also necessary to collect the image of the barcode, typically by means of a film camera or a camera, typically from the camera of a cell phone (smartphone).

The device of the present invention is therefore easily implemented, that is to say that it does not require any particular analysis technique: a simple control using a flash and a film camera or a camera is sufficient to analyze the response of the biosensor.

The mode of reading of the biosensor of the invention, using luminescence and preferably fluorescence, has the advantage of being discreet and confidential since only the user provided with a suitable light source and reading means, typically a smartphone equipped with a flash and the dedicated application, is able to decrypt the information encoded in the barcode of the biosensor.

In the medical field, for example in the case of the detection of a bacterial contamination in a patient, this reading mode allows the medical staff not to alarm the patient in case of infection.

As already described above, the analysis of the image of the barcode makes it possible to access various items of information, such as the presence or absence of a targeted biological agent and whether or not an infectious dose has been reached, as a function of the measured luminescence intensity, and also any other information integrated in the barcode such as the location of the detected infection, the identification of the pathogens, the estimation of the amount of pathogens to determine whether the infectious dose has been exceeded or not, or the programming of an antibiogram as a function of the type of bacteria identified.

Thus, several modes of reading the barcode may be envisaged, according to the embodiments of the invention:
- reading step, where the modified barcode itself encodes information regarding the presence of a targeted biological agent,
- reading step followed by a comparison with the initial barcode to identify the areas of the barcode that appear modified, making it possible to draw conclusions regarding the presence or absence of targeted biological agents, or
- reading step followed by a step of measuring the contrast of the areas of the barcode that appear modified, and comparison with calibration values, making it possible to draw conclusions regarding the concentration of targeted biological agents.

According to another subject, the present invention relates to the use of a biosensor according to the invention for analyzing contamination by at least one biological agent in an environment.

The biosensor of the invention is suitable for detecting contamination by at least one biological agent in a patient in a hospital environment, in a foodstuff, in the agricultural or horticultural field, or in the field of water treatment.

The biosensor of the invention is particularly suitable for detecting bacterial contamination in a patient by analyzing their body fluids such as their blood, sweat, urine, or saliva.

The biosensor of the invention is also particularly suitable for determining if an infectious dose has been exceeded.

According to another subject, the present invention relates to a device for analyzing contamination by at least one biological agent in an environment, comprising at least one biosensor according to the invention.

The present invention is further illustrated by the following examples, without being limited thereto.

EXAMPLES

Example 1

General Protocol for Attaching the Aptamers and the Dye

Equipment
Agitator and plate (Vortex)
Precision balance
Hotplate
Corona surface treatment machine
Reagents
3-mercaptopropionic acid (MPA), Sigma Aldrich
N-hydroxysuccinimide (NETS), Sigma Aldrich
1-ethyl-3-(3-dimethylaminopropyl) carbodiimide (EDC), Sigma Aldrich
deionized water and distilled water, IES
[cephalosporin]-[ATTO], Sigma Aldrich (reference: C0682000-97875)
Step 1—Preparing the Support
Thermal Evaporation of Aluminum Under Vacuum A crucible filled with aluminum metal was heated until the aluminum evaporated. Facing the crucible, a paper substrate was placed so as to condense the aluminum vapors on said substrate.

An aluminum layer approximately 1 µm thick was obtained.

Anodization

In a tank filled with 15% phosphoric acid, at a temperature of 0° C.-5° C., the substrate coated with an aluminum layer obtained in the previous step was placed at the anode of a generator of direct current, the cathode of the system being made of platinum (inert in the middle).

A voltage of between 80 V-120 V was applied and the substrate was immersed for a period of from 600 s to 900 s to form a layer of alumina on the surface of the aluminum deposit. For 600 s: thickness=425 nm-450 nm and pore size=81 nm-96 nm. For 900 s: thickness=800 nm-950 nm and pore size=81 nm-96 nm.

Cleaning the Support

The support was then cleaned by submerging it in deionized water at 70° C. for 1 minute and then in deionized water at 20° C. for 1 minute.

Surface Treatment (Corona Effect)

The alumina surface of the cleaned support was then treated by corona effect for 30 seconds. This treatment makes it possible to improve the wettability and surface tension (adhesion) of the alumina surface and also makes it possible to protect it against corrosion.

Step 2: Activation of the Surface of the Support

It is necessary to activate the outer surface of the alumina layer of the support to prepare the grafting of the aptamers.

A conventional method of molecular self-assembly (self-assembly monolayer), especially described in Wu et al. (PLOS ONE 2012, 7(11), 1-9) or in Braiek et al. (Biosensors 2012, 2, 417-426) was used to coat the outer surface of the alumina layer of the support with —O-succinimide labile groups.

For this, MPA (30 µl of a 100 mM solution) was first deposited on the alumina surface, then the support thus coated was left stirring (plate vortex agitator) for 1 hour at room temperature.

The alumina layer, initially grafted with —OH groups, is thus grafted with —S—CH$_2$CH$_2$—C(O)—OH groups.

After washing the surface thus functionalized with distilled water, 30 µl of a mixture of EDC/NHS (solution containing 100 mM EDC and 50 mM NHS, previously prepared and stirred for 1 hour) was deposited on the surface, then the support coated in this way was left stirring (plate vortex agitator) for 1 hour at room temperature.

The alumina layer is thus grafted with —S—CH$_2$CH$_2$—C(O)—O-succinimide groups, the —S—CH$_2$CH$_2$—C(O)— chain corresponding to a first spacer.

Step 3

First Variant: Successive Attachment of the Aptamers and the Dye

According to a first variant, referred to as "linear", the aptamers are first attached to the support, then the dye is grafted to the aptamers.

Aqueous solutions of aptamers (concentration of 1 µmol/ml aptamer) were prepared.

Depending on the type of bacteria that it is desired to detect, an associated aptamer is used.

The following table indicates an associated aptamer (single DNA strand):

| Bacterial strain | Aptamer |
|---|---|
| Escherichia coli ATCC 8739 | 5'CGC GTC CCC CGC CGG GCG CGC GCC AGG ATC GAC 3' (SEQ ID NO: 1) |
| Escherichia coli 0157 H7 | 5'CTT CTG CCC GCC TCC TTC CTA GCC GGA TCG CGC TGG CCA GAT GAT ATA AAG GGG TCA GCC CCC CAG GAG ACG AGA TAG GCG GAC ACT 3' (SEQ ID NO: 2) |
| Staphylococcus aureus | 5'TCC CTA CGG CGC TAA CGC CAC CGT GCT ACA ACT CGG ATT 3' (SEQ ID NO: 3) |
| Escherichia coli 0157 H7 | 5'GTC TGC GAG CGG GGC GCG GGC CCG GCG GGG GAT GCG 3' (SEQ ID NO: 4) |

The 3' ends of the aptamers used are preferably —COOH group-modified beforehand by a technique known to those skilled in the art.

Alternatively, the 5' ends of the aptamers used may be $NH_2$ group-modified by a technique well known to those skilled in the art.

In order to functionalize a specific area of the surface of the support, use may be made of a mask suited to the dimensions of the support and having at least one opening that coincides with the area of the support that it is desired to functionalize when the mask is superimposed on the support. This mask may have several openings that correspond to the different areas to be functionalized, by the same aptamer or preferably by different aptamers so as to be able to immobilize different infectious agents.

Thus, when it is desired to functionalize one or more areas with one or more aptamers, a mask suited to the dimensions of the support and having as many openings as areas to be functionalized is superimposed, then the aptamer solution(s) are deposited in the corresponding opening(s) by any means known to those skilled in the art, and in the same step.

In addition to the use of a mask, other techniques known to those skilled in the art may also be used, such as inkjet printing. To this end, aptamer solutions are provided as inks of the inkjet printer and the areas of the support to be functionalized are successively printed.

Regardless of the technique used, after the deposition of one or more aptamers, the support thus coated is then left stirring (plate vortex agitator) for 30 minutes at room temperature, then stirring is stopped and the support is placed under a fume hood for 30 minutes.

An aptamer molecule (single strand of DNA) is thus attached by an —$NH_2$ group borne by one of its bases (adenine, guanine or cytosine) to an —S—$CH_2CH_2$—C(O)—O— succinimide group. An amide bond —C(O)—NH— is formed, and an N-hydroxysuccinimide molecule leaves.

The deposition of the aptamer solutions may be repeated 1 or 2 more times so as to optimize the degree of grafting, then the support is left overnight at room temperature and is finally rinsed with distilled water.

After the attachment of the aptamers to the support, the dye is then grafted to the aptamers.

The dye is preferably provided in the form of a precursor, containing a first unit corresponding to the dye and a second unit corresponding to a second spacer, these two units being covalently bonded.

As dye precursor, use is preferably made of the compound [cephalosporin]-[ATTO] (Sigma Aldrich), in which the [cephalosporin] unit denotes the second spacer and comprises a free —$NH_2$ group, and the [ATTO] unit denotes the dye.

Attachment of the compound [cephalosporin]-[ATTO] is carried out by first depositing, on a specific area of the support previously functionalized with aptamers, the coupling agent EDC (10 µl), which makes it possible to activate the free —COOH group of the 3' end of the aptamers. The support is stirred gently on a vortex plate for approximately 30 minutes and 20 µl of [cephalosporin]-[ATTO] complex are deposited on said area.

The dye is thus attached to the aptamer by creating a peptide bond between the free —$NH_2$ group of the [cephalosporin] unit and the free —COOH group of the 3' end of the aptamers.

Second Variant: One-Step Attachment of the Aptamer and the Dye

According to a second variant, referred to as "convergent", the dye is first grafted onto the aptamer, then this complex is subsequently attached to the support.

This variant may be adapted from the first variant, by first carrying out the coupling of the aptamer and the dye away from the support.

As aptamer, use is preferably made of the aptamers described above, the 3' ends of which are preferentially —COOH group-modified beforehand by a technique known to those skilled in the art.

As dye, use is preferably made of the compound [cephalosporin]-[ATTO] described above.

The coupling between an aptamer and the [cephalosporin]-[ATTO] dye may be carried out by peptide coupling according to a method known to those skilled in the art.

The aptamer-[cephalosporin]-[ATTO] complex may subsequently be grafted onto the surface of the support, previously functionalized with —S—$CH_2CH_2$—C(O)—O— succinimide groups by a method similar to that employed in the first variant.

Example 2

Producing a 2D Barcode Biosensor

A 2D barcode biosensor was produced using the protocol of example 1.

First, the alumina supports are produced.

Then, the barcode pixels are printed, leaving blank the areas intended to be functionalized by the aptamers and the dye.

Finally, the aptamers were grafted onto the predetermined specific areas.

A biosensor capable of detecting both *Escherichia coli* ATCC 8739 and *Staphylococcus aureus* was especially prepared using the aptamers described above and the [cephalosporin]-[ATTO] dye.

Example 3

Implementing a 2D Barcode Biosensor

Four identical 2D barcode biosensors, manufactured in example 2 and capable of detecting *Escherichia coli* ATCC 8739 and *Staphylococcus aureus* were tested by applying, to each of the 2D barcodes:
- a control sample solely comprising physiological saline,
- a sample no. 1 comprising *Escherichia coli* ATCC 8739 at a concentration of $10^6$ CFU in physiological saline,
- a sample no. 2 comprising *Staphylococcus aureus* at a concentration of $10^4$ CFU in physiological saline, or
- a sample no. 3 comprising *Escherichia coli* ATCC 8739 at a concentration of $10^6$ CFU and *Staphylococcus aureus* at a concentration of $10^4$ CFU in physiological saline.

After applying the samples no difference in code was detectable to the naked eye.

The 2D barcodes of the three biosensors were photographed with a smartphone equipped with a flash (wavelength 640 nm to 670 nm).

In the barcode picture of the control sample, no difference was identified with the initial code.

On the other hand, in the photo of the barcode of the sample no. 1, the code appeared modified compared to the initial code; the area functionalized by the aptamer specific to *Escherichia coli* ATCC 8739 appeared colored.

Similarly, in the photo of the barcode of the sample no. 2, the code appeared modified compared to the initial code; the area functionalized by the aptamer specific to *Staphylococcus aureus* appeared colored.

As for the photo of the barcode of the sample no. 3, the code also appeared modified compared to the initial code; the areas functionalized by the aptamer specific to *Escherichia coli* ATCC 8739 and by the aptamer specific to *Staphylococcus aureus* both appeared colored.

Comparison of the code photographed by the smartphone with a reference code, preferably stored in the smartphone, thus made it possible to determine the presence or absence of a bacterium in the sample, as well as the type of bacteria.

Measurement of the color contrast that appears on the photo of the code, compared to previously stored calibration values, also made it possible to determine the concentration of bacteria in each of the samples no. 1, no. 2 and no. 3.

Example 4

Embodiment Example with 1D and 2D Barcode Using a Chromogenic Antibiotic as Coloring Molecule In this example, the biosensor as produced in example 5 below is used.

4.1. Producing a 2D Barcode

FIG. 3 illustrates the visual change in a 2D barcode by change of color hue before and after a target bacterium is revealed by a biosensor according to the invention.

The following observations are made:
- in (a), the base matrix of the 2D barcode. It is formed of small squares.
- in (b), the 2D barcode contains information; for example, in this case, "neg" (for negative). This is made possible because there is a contrast between the small yellow squares (dark) and the white squares (light).

Some small squares (white or yellow) have been functionalized by the process described above. Contact with a liquid biological sample such as saliva, urine, blood, perspiration or any preparations using such samples.

- in (c), the 2D barcode is functionalized to detect one or more target bacteria and is used as described above. In the present case, this 2D barcode detects the absence of target bacteria.
- in (d), a 2D barcode functionalized to detect one or more target bacteria is used as described above. In the present case, the 2D barcode detects the presence of target bacteria; namely, the small functionalized squares change hue (the dark squares may become light, or vice versa).

In the present case, the small yellow or white squares become red. As a result, the small yellow and white squares become the "light" squares and the small red squares become the "dark" squares. Consequently, the message carried by the 2D barcode has changed. The contrast thus produced makes it possible to read "pos" for positive.

4.2. Producing a 1D Barcode

FIG. 4 illustrates the visual change in a 1D barcode by change of color hue before and after a target bacterium is revealed by a biosensor according to the invention.

The following observations are made:
- in (a), namely before bringing the bacterium into contact with the biosensor, the base matrix of the 1D barcode is formed of dark or light rectangles.
- in (b), the 1D barcode contains information; for example, in this case, "neg" (for negative). This is made possible because there is a contrast between the yellow rectangles (dark) and the white rectangles (light).

Some rectangles (white or yellow) have been functionalized by the process described above.

- in (c), the biosensor is functionalized to detect one or more target bacteria and is used as described above. In the present case, the 1D barcode just detects the presence of a target bacterium. The rectangles remain yellow. Thus, this 1D barcode detects the absence of target bacteria.
- in (d), the functionalized biosensor is used and reacts positively; namely, the functionalized rectangles have changed hue (the dark rectangles may become light, and vice versa).

In the present case, the yellow or white rectangles become red. As a result, the yellow and white rectangles become the "light" rectangles and the red rectangles become the "dark" rectangles. Consequently, the message carried by the 1D barcode has changed. The contrast thus produced makes it possible to read "pos" for positive.

Example 5

Implementing a Flexible Plastic Biosensor

The biosensor described in this example illustrates the variant of the invention in which a coloring molecule comprises a chromogenic antibiotic, in the present example from the class of the cephalosporins: nitrocefin, this variant not requiring the presence of a second spacer. No labile bond breakage occurs following the attack of the β-lactamase on the lactam ring of the antibiotic.

Equipment
Agitator and plate (Vortex)
Precision balance
Hotplate
Corona surface treatment machine
Reagents
3-(Trimethoxysilyl)propyl methacrylate (TPM), Sigma Aldrich
Sodium hydroxide (NaOH), Sigma Aldrich
deionized water and distilled water, IES
  Nitrocefin, Sigma Aldrich
  Aptamer: $E\ coli$ 0157: H7 modified at its 5' end with NH2
  Dimethyl sulfoxide (DMSO), Sigma Aldrich
  Lactamator: Beta lactamase solution, CPC Biotech
Step 1—Preparing the Support
In one example, the functionalized support is a flexible plastic support, Teslin, a hydrophobic and synthetic substrate which has the advantage of being very strong, while being very thin.

As above (example 1), a corona pre-treatment is carried out for 5 minutes.

OH groups are subsequently added to the surface of the substrate using a bath of sodium hydroxide at low concentration (<20%) before being rinsed with distilled water.

Step 2: Grafting the Aptamer Using a Linker

This immobilization technique is based, as above (example 1) on the principle of self-assembled monolayers, formed here of an organosilane, TPM.

This step requires several hours of incubation (1 h to 6 h) and was tested for concentrations between 10 and 50 mM. The incubation is carried out under a fume hood, with stirring and at room temperature. In order to eliminate the molecules that have not been grafted, rinsing with distilled water is carried out.

The attachment of the aptamer to the TPM follows. The 5' end of the aptamer was modified with an amine group ($NH_2$) by a technique known to those skilled in the art. The aptamers are subsequently added to the sample in accordance with the protocol followed in example 1.

The sample is subsequently rinsed with distilled water in order to eliminate the aptamers that have not specifically bound the TPM.

Step 3: Attaching the Dye

The aptamer tested (SEQ ID NO: 4) ends with a guanine base, which naturally has a free $NH_2$ group at its end (since the aptamer is single-stranded, the $NH_2$ group is not involved in hydrogen bonding with a cytosine, as is the case in a double-stranded configuration).

This $NH_2$ group is used for attaching the coloring molecule. In this example, coloring molecule denotes a chromogenic antibiotic of the class of the cephalosporins: nitrocefin. The use of a chromogenic antibiotic is the variant tested here, because it makes it possible to eliminate an additional step and simplifies color detection (visible to the naked eye).

Different concentrations of nitrocefin have been tested to date (5 to 30 mM).

After incubation (30 minutes to 3 hours), the sample is rinsed with DMSO. At the end of this step, a yellow color appears on the support.

Step 4: Colorimetric Test and Specificity

A first test is performed to ensure the presence of nitrocefin on the surface of the functionalized substrate: a few tens of microliters of β-lactamase solution are deposited. A red coloration is then observed on the surface of the substrate, suggesting that there was indeed binding of the nitrocefin to the molecular construct grafted on the substrate.

A second test is performed to verify that, in the absence of the molecular construct described above, the nitrocefin is eliminated during rinsing with DMSO. The test is performed after two different steps (step 1 and step 2). In both cases, the addition of β-lactamase does not cause a colorimetric reaction.

---

The invention claimed is:

1. A biosensor for detecting the presence and/or measuring the concentration of at least one biological agent, comprising a support on which a barcode is placed, at least one area of which is functionalized by at least one aptamer capable of selectively immobilizing said biological agent, said aptamer itself being linked, directly or indirectly, to a coloring molecule, wherein:
   said coloring molecule is linked via a labile bond to the aptamer and is able to produce color following an enzyme attack causing a break of said labile bond; or, alternatively,
   said coloring molecule is an antibiotic covalently bonded to the aptamer and is able to produce color or to change color following the immobilization of the biological agent by said aptamer.

2. The biosensor as claimed in claim 1, wherein the support is a flexible or rigid support on which the barcode is placed.

3. The biosensor as claimed in claim 1, wherein the support is made of glass, paper or plastic.

4. The biosensor as claimed in claim 3, wherein a layer of alumina is placed on the support.

5. The biosensor as claimed in claim 1, wherein the barcode is a one-dimensional barcode composed of an assembly of parallel black stripes and white stripes in which at least one area of at least one white stripe or black stripe is functionalized by at least one aptamer.

6. The biosensor as claimed in claim 1, wherein the barcode is a 2-dimensional barcode composed of an assembly of black pixels and white pixels, in which at least one white pixel or at least one black pixel is functionalized by at least one aptamer.

7. The biosensor as claimed in claim 1, wherein the aptamer capable of selectively immobilizing said biological agent is an RNA strand, a DNA strand or a peptide, the 3' end of which is modified to bear a —COOH function, or else the 5' end of which is modified to bear an —NH$_2$ function.

8. The biosensor as claimed in claim 1, wherein the aptamer is covalently bonded to the barcode area via a first spacer.

9. The biosensor as claimed in claim 1, wherein the biological agent is selected from the group consisting of bacteria, prions and viruses, mycotoxins and peptides.

10. The biosensor as claimed in claim 1, wherein the biological agent is a bacterium and the aptamer is capable of selectively binding at least one membrane protein of said bacterium.

11. The biosensor as claimed in claim 1, wherein the biological agent is a bacterium selected from the group consisting of *Escherichia coli*, *Pseudomonas aeroginosa*, *Acinetobacter baumannii*, *Staphylococcus aureus*, *Clostridium difficile*, *Clostridium botulinum*, *Streptococcus pneumoniae*, *Treponema pallidum*, *Salmonella gastroenteretis*, *Listeria monocytogenes* and *Legionella* spp.

12. The biosensor as claimed in claim 1, wherein said coloring molecule is non-luminescent and may be selected from a chromogenic antibiotic or is luminescent, and may be selected from 5-FAM, 6-FAM, ATTO type dyes, especially ATTO 532 or ATTO 550, ATTO 647, DY-510XL, DY-530, HEX, CAL Fluor Orange 560.

13. The biosensor as claimed in claim 1, wherein said coloring molecule is non-luminescent in its form linked to the aptamer and luminescent, in its form not linked to the aptamer.

14. The biosensor as claimed in claim 13, wherein the coloring molecule has a light absorption band of from 600 nm to 700 nm, and a light emission band of from 600 nm to 700 nm or a minimum colorimetric shift for detection.

15. The biosensor as claimed in claim 8, wherein the coloring molecule is covalently bonded to the aptamer via a second spacer, said second spacer being linked to the coloring molecule by a labile chemical bond which is capable of breaking following immobilization of the biological agent by the aptamer.

16. The biosensor as claimed in claim 15, wherein the second spacer is a divalent radical comprising a β-lactam unit.

17. A process for analyzing contamination by at least one biological agent in an environment, comprising at least the steps consisting in:
   making available a biosensor as claimed in claim 1,
   bringing the biosensor into the presence of the environment to be analyzed, under conditions conducive to the immobilization of the biological agent(s) which may be present in said environment by the aptamers of the biosensor,
   reading the biosensor thus coated, so as to acquire the information encoded by the barcode of the biosensor thus coated, and
   generating, from the acquired information, information regarding the possible presence of at least one biological agent in the environment.

18. A method for analyzing contamination by at least one biological agent in an environment comprising using a biosensor as claimed in claim 1.

19. A device for analyzing contamination by at least one biological agent in an environment, comprising at least one biosensor as claimed in claim 1.

20. The biosensor as claimed in claim 8, wherein the first spacer is a spacer of formula —S—$(CH_2)_n$—C(O)— where n is an integer from 2 to 6 and wherein the sulfur atom is covalently bonded to the support and the carbon atom of the C(O) group is covalently bonded to a nitrogen atom of the aptamer or is bonded by a silane bond (OH-Silane-$NH_2$), by a heterobifunctional linker (heterobifunctional SH-linker-$NH_2$), or else by UV.

21. The biosensor as claimed in claim 1, wherein the support is made of microporous polyethylene or polypropylene.

22. The biosensor as claimed in claim 1, wherein the biological agent is chosen from lipopolysaccharides (LPS) and peptidoglycans (PPG).

23. The biosensor as claimed in claim 8, wherein the coloring molecule is covalently bonded to the aptamer via a second spacer, said second spacer being linked to the coloring molecule by a labile chemical bond capable of breaking in the presence of a β-lactamase.

24. The biosensor as claimed in claim 15, wherein the second spacer is a divalent radical comprising a cephalosporin unit.

25. The biosensor as claimed in claim 1, wherein the coloring molecule is an antibiotic covalently bonded to the aptamer, said coloring molecule comprising a chromogenic antibiotic.

26. The biosensor as claimed in claim 1, wherein the coloring molecule is an antibiotic covalently bonded to the aptamer, said coloring molecule being selected from cephalosporins and penicillins.

27. The biosensor as claimed in claim 1, wherein said coloring molecule is ATTO.

* * * * *

SEQUENCE LISTING

<160> NUMBER OF SEQ ID NOS: 4

<210> SEQ ID NO 1
<211> LENGTH: 33
<212> TYPE: DNA
<213> ORGANISM: Escherichia coli ATCC 8739
<220> FEATURE:
<223> OTHER INFORMATION: Aptamere

<400> SEQUENCE: 1
cgcgtccccc gccgggcgcg cgccaggatc gac        33

<210> SEQ ID NO 2
<211> LENGTH: 87
<212> TYPE: DNA
<213> ORGANISM: Escherichia coli O157:H7
<220> FEATURE:
<223> OTHER INFORMATION: Aptamere

<400> SEQUENCE: 2
cttctgcccg cctccttcct agccggatcg cgctggccag atgatataaa ggggtcagcc        60
ccccaggaga cgagataggc ggacact        87

<210> SEQ ID NO 3
<211> LENGTH: 39
<212> TYPE: DNA

```
<213> ORGANISM: Staphylococcus aureus
<220> FEATURE:
<223> OTHER INFORMATION: Aptamere

<400> SEQUENCE: 3
tccctacggc gctaacgcca ccgtgctaca actcggatt                         39

<210> SEQ ID NO 4
<211> LENGTH: 36
<212> TYPE: DNA
<213> ORGANISM: Escherichia coli O157:H7
<220> FEATURE:
<223> OTHER INFORMATION: aptamere

<400> SEQUENCE: 4
gtctgcgagc ggggcgcggg cccggcgggg gatgcg                            36
```